United States Patent
Namima et al.

(10) Patent No.: US 12,426,852 B2
(45) Date of Patent: Sep. 30, 2025

(54) CATHETER WITH ACOUSTIC LENS ARRANGEMENT FOR LOCALIZED ULTRASONIC WAVE TRANSMISSION

(71) Applicant: ASAHI INTECC CO., LTD., Seto (JP)

(72) Inventors: Satoshi Namima, Seto (JP); Fumiyoshi Oshima, Seto (JP); Yuta Kubo, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 138 days.

(21) Appl. No.: 17/980,904

(22) Filed: Nov. 4, 2022

(65) Prior Publication Data

US 2023/0057999 A1 Feb. 23, 2023

Related U.S. Application Data

(63) Continuation of application No. PCT/JP2021/015651, filed on Apr. 16, 2021.

(30) Foreign Application Priority Data

May 15, 2020 (JP) .................................. 2020-086021

(51) Int. Cl.
*A61B 8/00* (2006.01)
*A61B 8/12* (2006.01)

(52) U.S. Cl.
CPC .................. *A61B 8/445* (2013.01); *A61B 8/12* (2013.01); *A61B 8/4494* (2013.01)

(58) Field of Classification Search
CPC ......... A61B 8/445; A61B 8/12; A61B 8/4494; A61B 8/4477; G01S 15/8913; G01S 15/8922
See application file for complete search history.

(56) References Cited

U.S. PATENT DOCUMENTS 10,092,271 B2 * 10/2018 Lewis, Jr. ............ A61B 8/0866
2007/0232921 A1 * 10/2007 Lee ....................... B06B 1/0655
600/459

(Continued)

FOREIGN PATENT DOCUMENTS

CN        101208045 A     6/2008
JP       2019-122657 A    7/2019
(Continued)

OTHER PUBLICATIONS

Translation of KR-20180096849-A (Year: 2018).*

*Primary Examiner* — Christopher L Cook
*Assistant Examiner* — Dean N Edun
(74) *Attorney, Agent, or Firm* — Oliff PLC (57) ABSTRACT

A catheter includes a transmission unit that is disposed at the distal end of a tube having a lumen and has an ultrasonic wave transmitting function; a reception unit that is disposed at the distal end of the tube and has an ultrasonic wave receiving function; and an acoustic lens that is disposed so as to cover only the transmission unit among the transmission unit and the reception unit. Ultrasonic beams transmitted from the transmission unit are converged by passing through the acoustic lens, and a reflected wave reflected on biological tissue is received by the reception unit without passing through the acoustic lens. Since setting of the positions, number, and the like of the reception units is not bound by the position, size, and the like of the acoustic lens, the positions, number, and the like of the reception units can be appropriately set to improve ultrasonic reception efficiency.

6 Claims, 6 Drawing Sheets

(56) References Cited

U.S. PATENT DOCUMENTS

| | | |
|---|---|---|
| 2007/0242567 A1 | 10/2007 | Daft et al. |
| 2015/0025518 A1 | 1/2015 | Kobayashi et al. |
| 2016/0374710 A1* | 12/2016 | Sinelnikov ......... A61B 17/3207 600/439 |
| 2019/0321110 A1* | 10/2019 | Grunwald ............ A61B 5/7271 |

FOREIGN PATENT DOCUMENTS

| | | | |
|---|---|---|---|
| KR | 20180096849 A * | 8/2018 | ........... A61B 8/4494 |
| WO | 2006/122001 A2 | 11/2006 | |

* cited by examiner

CATHETER WITH ACOUSTIC LENS ARRANGEMENT FOR LOCALIZED ULTRASONIC WAVE TRANSMISSION

CROSS REFERENCE TO RELATED APPLICATIONS

This is a Continuation of PCT/JP2021/015651 filed Apr. 16, 2021, which claims priority to JP 2020-086021 filed May 15, 2020. The disclosure of the prior applications is hereby incorporated by reference herein in its entirety.

TECHNICAL FIELD

The disclosed embodiments relate to a catheter.

BACKGROUND

Patent Literature 1 discloses, as an apparatus for examining morphology of biological tissue with ultrasonic waves, an ultrasonic probe that includes a concentric array oscillator having a concentric arrangement of ultrasonic oscillators, and an ultrasonic shield having an acoustic window with an opening in a radius direction. Ultrasonic waves transmitted from a concentric array oscillator are converged by passing through an acoustic lens of the acoustic window. Reflected waves reflected on biological tissue pass through the same acoustic lens and are received by the concentric array oscillator. On the basis of received information at the concentric array oscillator, the morphology of the biological tissue is imaged.

CITATION LIST

Patent Literature

Patent Literature 1: JP 2019-122657 A

SUMMARY

Technical Problem

The apparatus described above has a problem in that the reception range of reflected ultrasonic waves is limited to an opening region of a slit acoustic window, thus providing less amount of information on the basis of reception of the reflected ultrasonic waves. Particularly, when the irradiated ultrasonic wave is reflected by a biological tissue to a direction different from the direction toward the acoustic window, it is not possible to accurately capture a corresponding shape of the biological tissue from which the ultrasonic wave is reflected.

In addition to the apparatus described above, a configuration can also be contemplated that transmits ultrasonic waves from a plurality of transmission units and irradiates a converged ultrasonic wave. However, when each transmission unit irradiates an ultrasonic wave on biological tissue, which is an irradiated object, the difference in distance for conveying an ultrasonic wave from each transmission units to the biological tissue and other factors case a gap between phases of the ultrasonic waves each arrived at the biological tissue, and generate attenuation or amplification of the arriving ultrasonic waves.

The disclosed embodiments were completed on the basis of the circumstances described above, and have an objective to improve of reception efficiency of ultrasonic waves.

Solution to Problem

The disclosure provides the following:

(1) a catheter comprising: a transmission unit disposed at the distal end of a tube having a lumen, the transmission unit having an ultrasonic wave transmitting function, a reception unit disposed at the distal end of the tube, the reception unit having an ultrasonic wave receiving function, and an acoustic lens disposed so as to cover only the transmission unit among the transmission unit and the reception unit;

(2) the catheter according to the item (1), where the transmission unit(s) is localized at a limited area, and where the reception unit includes a plurality of reception units distributed at a plurality of locations;

(3) the catheter according to the item (1) or (2), where each of the transmission unit and the reception unit includes an oscillator having both of an ultrasonic wave transmitting function and an ultrasonic wave receiving function, and where the acoustic lens is capable of shifting relative to the transmission unit and the reception unit, in a manner of selectively covering only a part of the oscillators among a plurality of the oscillators;

(4) the catheter according to any one of the items (1) to (3), where at least the reception units among the transmission unit and the reception units are disposed so as to surround the lumen;

(5) the catheter according to any one of the items (1) to (4), where the transmission unit includes a first transmission unit and a second transmission unit arranged so as to interpose the lumen, and where the acoustic lens includes a first acoustic lens which covers the first transmission unit and a second acoustic lens which covers the second transmission unit; and (6) the catheter according to any one of the items (1) to (5), where the transmission unit has a row of a plurality of oscillators having an ultrasonic wave transmitting function.

Advantageous Effects

Ultrasonic beams transmitted from the transmission unit are converged by passing through an acoustic lens, and a reflected wave reflected on biological tissue is received by a reception unit without passing through the acoustic lens. Since setting of the positions, number, and the like of reception units is not bound by the position, size, and the like of the acoustic lens, the positions, number, and the like of reception units can be appropriately set to improve ultrasonic reception efficiency.

DETAILED DESCRIPTION OF EMBODIMENTS

In embodiments disclosed herein, the transmission unit(s) may be localized at a limited area, and the reception units may be distributed at a plurality of locations. An acoustic lens is disposed in the transmission unit, and ultrasonic waves transmitted from the transmission unit are converged and irradiated on biological tissue, which is an irradiated object, thereby allowing improvement in energy density of ultrasonic. This configuration allows, in biological tissue, energy of ultrasonic waves transmitted from the transmission unit to have reduced attenuation or amplification due to any difference in the distance of a route for propagating the ultrasonic waves. In addition, reflected waves reflected on biological tissue and spreading in various directions can be received by a plurality of reception units, thus improving resolution of an image of the biological tissue acquired on the basis of received information at the reception units.

Each of the transmission unit and the reception unit may include an oscillator that has both of an ultrasonic wave transmitting function and an ultrasonic wave receiving function, and the acoustic lens may be capable of shifting relative to the transmission unit and the reception unit, in a manner of selectively covering only a part of the oscillators among a plurality of the oscillators. This configuration allows irradiation of ultrasonic waves on one biological tissue from a plurality of positions by relative shift of an acoustic lens. In this way, a plurality of reception units can provide multifaceted received information even when the biological tissue has a complex morphology. This allows improvement in resolution of an image of biological tissue acquired on the basis of received information at reception units.

At least the reception units among the transmission unit and the reception units may be arranged so as to surround the lumen. Such a configuration can provide multifaceted received information on biological tissue that is a subject to be treated/examined by a medical device inserted in a lumen. This allows improvement in resolution of an image of biological tissue acquired on the basis of received information at the reception units.

The presence of a first transmission unit and a second transmission unit may be arranged so as to interpose the lumen, the first transmission unit may be covered with a first acoustic lens, and the second transmission unit may be covered with a second acoustic lens. Such a configuration can irradiate two ultrasonic waves from two opposite directions on biological tissue that is a subject to be treated/examined by a medical device inserted in a lumen. This allows acquisition of multifaceted received information even when the biological tissue has a complex morphology. This allows improvement in resolution of an image of biological tissue acquired on the basis of received information at reception units.

The transmission unit may have a row of a plurality of oscillators having an ultrasonic wave transmitting function. Such a configuration can converge a plurality of ultrasonic waves to form a converged ultrasonic wave, when different timing of ultrasonic wave transmission is made among the plurality of oscillators. The convergence position of the plurality of ultrasonic waves can be freely altered by changing the timing of ultrasonic wave transmission, thus allowing acquisition of much information on biological tissue.

Figure 1:
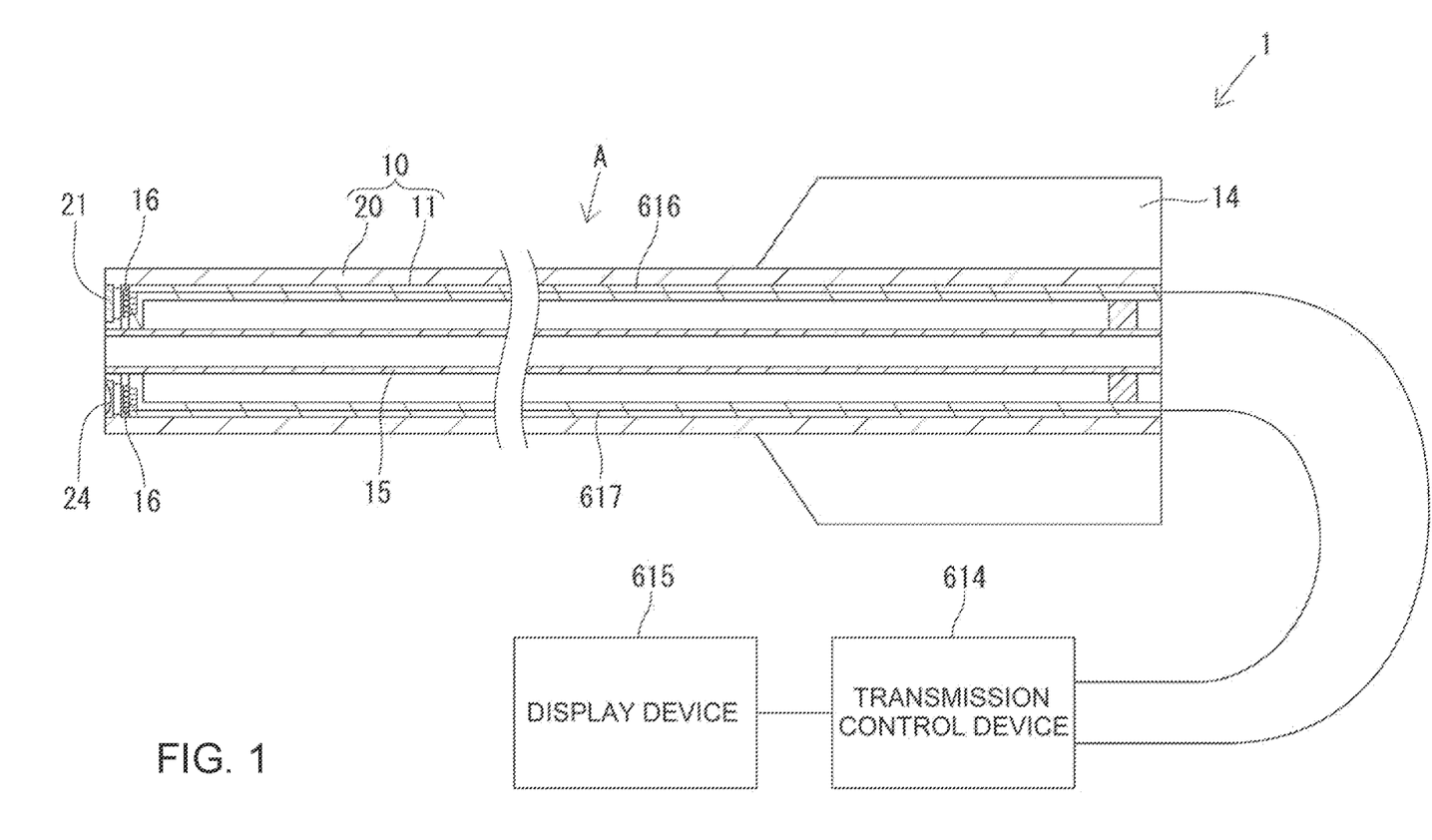
FIG. 1 is a front elevation view of a catheter of the disclosed embodiments.
Figure 2:
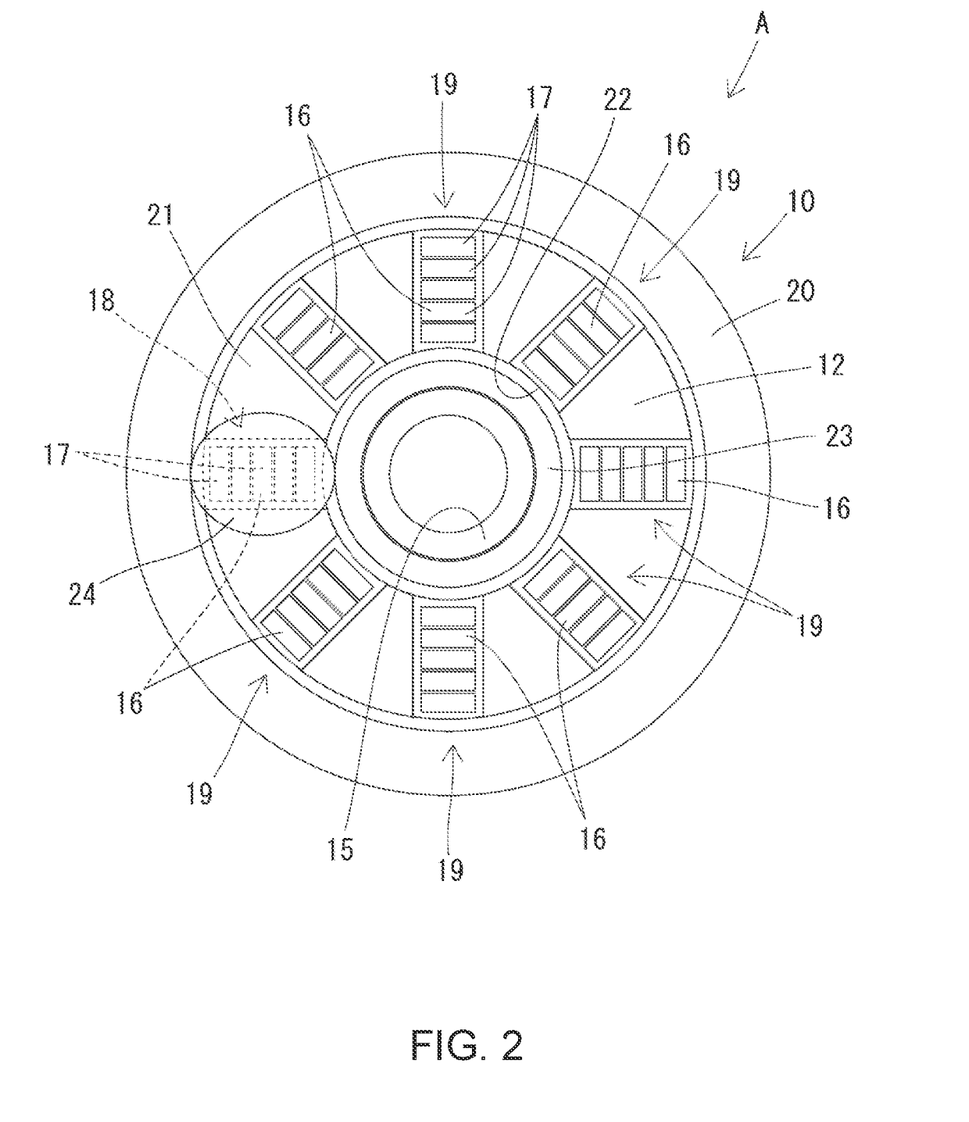
FIG. 2 is a front elevation view of the catheter.
Figure 3:
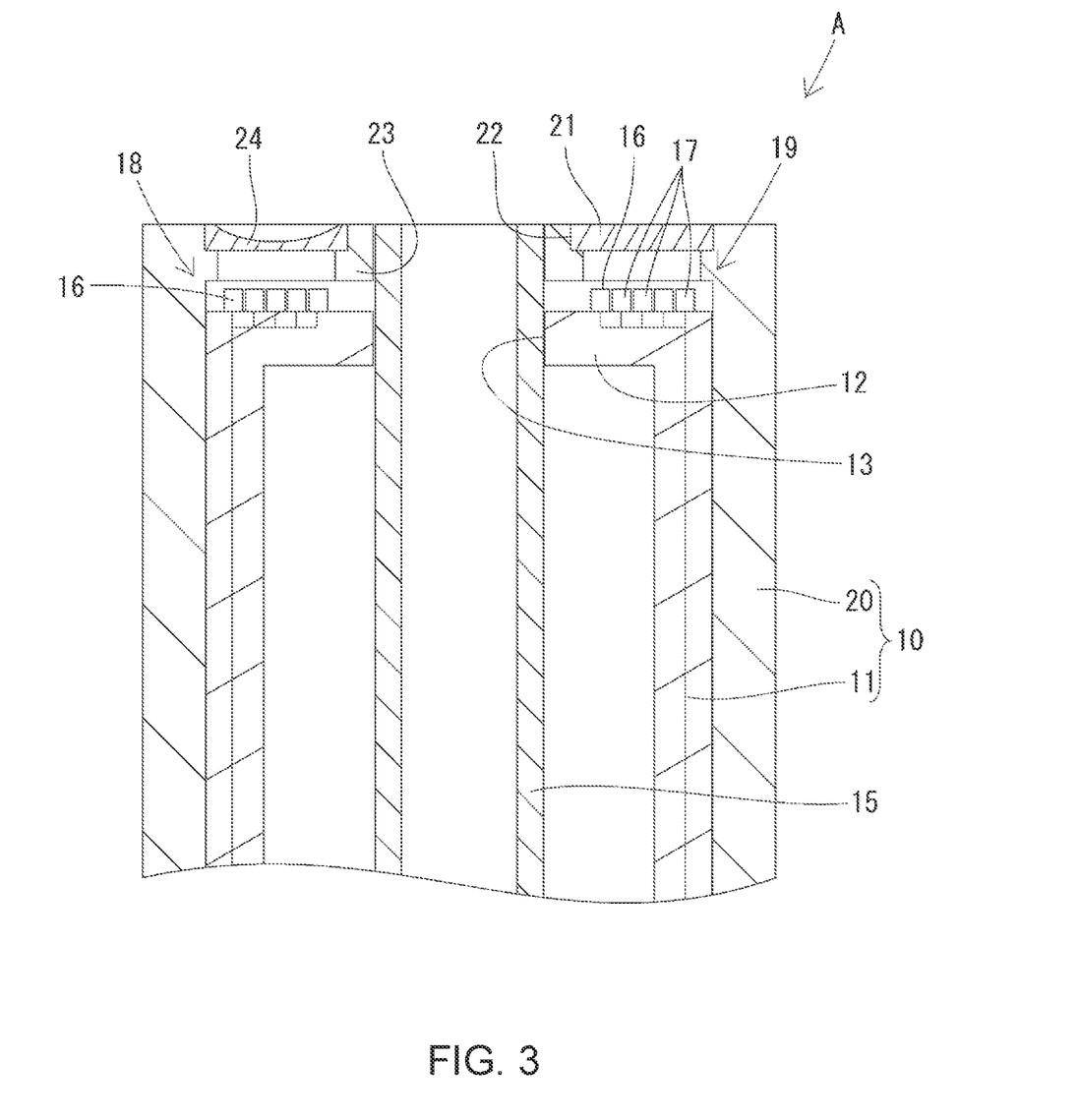
FIG. 3 is a sectional side view of the catheter.

An exemplary embodiment will now be described with reference to FIG. 1-FIG. 3. FIG. 1 shows a side sectional view of a catheter system 1 including a catheter A, a transmission control device 614, and a display device 615, and FIG. 2 shows a front elevation view, which is a front view of the catheter A. The catheter system 1 is not limited to the embodiment shown in FIG. 1-FIG. 3. With respect to a front-back direction, the description hereinafter defines upward in FIG. 3 as forward. The front end and the distal end in the catheter A are used synonymously.

The catheter A has one tube 10, which has flexibility, a lumen 15, which is formed inside the tube 10, eight ultrasonic sensors 16, and one acoustic lens 24. As shown in FIG. 1, the catheter system 1 includes the catheter A, a transmission control device 614, which controls the ultrasonic sensors 16, a display device 615, which displays information acquired from the ultrasonic sensors 16, and a connector 14 for facilitating a procedure of inserting the catheter A into the body, which incorporates signal lines 616 and 617 connecting the ultrasonic sensors 16 with the transmission control device 614.

The tube 10 has a form containing coaxially a long inner tube 11 inside a long outer tube 20, with the inner tube 11 and the outer tube 20 being restricted to relatively shift with respect to each other in a radial direction. The inner tube 11 and the outer tube 20 are configured to be capable of relatively rotating in a circumferential direction and closely sliding within the coaxial form, by way of manipulation at the proximal end of the catheter A, such as rotational manipulation of the connector 14. The lumen 15 has a circular shape in a cross section, and the lumen 15 is concentrically inserted in the inner tube 11. The lumen 15 is configured to receive insertion of a medical device such as a guide wire (depiction omitted).

The inner tube 11 has a circular shape in a cross section when cut perpendicular to the longitudinal direction. As shown in FIG. 3, the distal end of the inner tube 11 is integrally formed with a support plate portion 12, which forms a circular shape concentric with the inner tube 11. The outer peripheral edge of the support plate portion 12 is connected to the inner periphery of the inner tube 11. In the center of the support plate portion 12, a guide hole 13 is formed as a pass-through in a circular form concentric with the support plate portion 12. To the inner peripheral face of the guide hole 13, the lumen 15, formed inside the inner tube 11, is connected to form a pass-through.

The eight ultrasonic sensors 16 are attached to the front face of the support plate portion 12, i.e., a face on the distal end side in the support plate portion 12. In a front view as the catheter A is seen from the distal end side in the longitudinal direction (see FIG. 2), the eight ultrasonic sensors 16 are arranged concentrically at intervals of equal angle pitch in a circumferential direction with respect to the center of the guide hole 13. Each of the ultrasonic sensors 16 is configured to include a row of a plurality of oscillators 17 in a radial direction. The plurality of the oscillators 17 are radially arranged with respect to the center of the guide hole 13. Each of the oscillators 17 is formed of a piezoelectric element with use of a piezoelectric substance such as lead zirconate titanate (PZT). The oscillator 17 may employ not only PZT but also a polymer substance such as PVDF (polyvinylidene difluoride) and MEMS (microelectromechanical systems) device such as CMUT (capacitive micromachined ultrasonic transducers).

The oscillator 17 has both of a transmitting function to transmit ultrasonic waves by application of voltage and a receiving function to generate voltage by receiving ultrasonic waves. All the ultrasonic sensors 16 can therefore be switched between functioning as the transmission unit 18, which transmits ultrasonic waves, and the reception unit 19, which receives ultrasonic waves.

The oscillator 17 in seven of the ultrasonic sensors 16 functioning as the reception units 19 receives an ultrasonic wave reflected on biological tissue (depiction omitted). The time period from transmission of an ultrasonic wave by the transmission unit 18 to reception of a reflected wave by the oscillators 17 of the reception unit 19 is determined by a distance from the transmission unit 18 mainly to the biological tissue. The intensity of the reflected wave reflected on the biological tissue varies depending on composition and morphology of the biological tissue, which is a subject to be irradiated with the ultrasonic wave. The oscillator 17, upon receiving the ultrasonic wave, generates a voltage corresponding to the intensity of the reflected wave. On the basis of the voltage generated by the oscillator 17, an ultrasonic image (depiction omitted) of the biological tissue can be obtained.

The outer tube 20 has a circular shape in a cross section when cut perpendicular to the longitudinal direction. A disc plate 21 is fixed to the distal end of the outer tube 20 so as to be concentric with the outer tube 20 and to be capable of integrally rotating with the outer tube 20. The board thickness direction of the plate 21 is parallel to the longitudinal direction of the outer tube 20. The plate 21 has a central hole 22. An annular guide ring 23 is fixed to the central hole 22. To the guide ring 23, the distal end of the lumen 15 is connected to form a pass-through.

In the front view, the plate 21 forms concentrically with the support plate portion 12, and is disposed so as to cover the eight ultrasonic sensors 16 from the front side, i.e., the distal end side. The plate 21 is made of, e.g., silicone resin. The acoustic lens 24 is formed in the plate 21. In the front view, the acoustic lens 24 may form a substantially elliptic shape with a size to cover only any one of the ultrasonic sensors 16 among the eight ultrasonic sensors 16 from the front. The acoustic lens 24 forms a concave lens shape where a part of the front face of the plate 21 is recessed to have a curved surface. When the outer tube 20 and the inner tube 11 relatively rotate in a circumferential direction coaxially, the acoustic lens 24 and the eight ultrasonic sensors 16 relatively rotate.

The shape of the acoustic lens 24 is determined by the difference in speed between the sonic speed of an ultrasonic wave transmitted through a material of the plate 21, and the sonic speed of an ultrasonic wave in a medium such as blood in front of the plate 21. When the sonic speed in the plate 21 is lower than the sonic speed in a medium, the acoustic lens 24 is formed into a convex lens shape. When the sonic speed in the plate 21 is higher than the sonic speed in a medium, the acoustic lens 24 is formed into a concave lens shape.

When the catheter A is used to diagnose morphology of biological tissue, the inner tube 11 and the outer tube 20 are relatively rotated by way of manipulation at the proximal end of the catheter A. This manipulation causes the acoustic lens 24 to cover one of the ultrasonic sensors 16 to function as the transmission unit 18 among the eight ultrasonic sensors 16. Seven ultrasonic sensors 16, which are not covered with the acoustic lens 24, function as the reception units 19. In the front face of the distal end of the catheter A, one transmission unit 18 and seven reception units 19 are arranged at equal pitch in a circumferential direction.

The plurality of the oscillators 17, which together constitute the transmission unit 18, transmits ultrasonic waves by application of a voltage. The plurality of ultrasonic waves transmitted from the plurality of the oscillators 17 passes through the acoustic lens 24, and advances to the front of the catheter A, i.e., upward in FIG. 3. The acoustic lens 24 takes advantage of refractivity of ultrasonic waves to converge the plurality of ultrasonic waves. The ultrasonic waves thus converged form a single converged ultrasonic wave with high directivity. Since the converged ultrasonic wave has an intense energy, reflected waves reflected on biological tissue are received by the seven reception units 19 while holding an intense energy. On the basis of received information of ultrasonic wave acquired at the seven reception units 19, an ultrasonic image is created.

The ultrasonic image has higher resolution because the ultrasonic wave is irradiated with more intense energy on the biological tissue. In the present embodiment, ultrasonic waves transmitted from the transmission unit 18 are converged by the acoustic lens 24, and a converged ultrasonic wave with high energy is irradiated on biological tissue. The ultrasonic image has higher resolution also because the reception unit 19 provides a larger amount of received information. The amount of received information is larger, as the number of the reception units 19 is larger, and as an area including the reception units 19 is wider. In the present embodiment, the seven reception units 19 are arranged so as to surround the lumen 15, causing high reception efficiency of reflected waves and in turn, large amount of received information of the reflected waves. Accordingly, use of the catheter A allows acquisition of an ultrasonic image with high resolution.

A driving system for a plurality of the oscillators 17, which constitutes the transmission unit 18, can be a phased array system where a transmission voltage is applied to each oscillator constituting the plurality of the oscillators 17, with a little different timing. By controlling the plurality of the oscillators 17 in a phased array system, secondary waves of the ultrasonic waves transmitted from the plurality of the oscillators 17, which together constitute the transmission unit 18, can travel in a direction adjusted along a direction of arranging the plurality of the oscillators 17 (radial direction in this embodiment). Since such secondary waves pass through the acoustic lens 24 to be converged, ultrasonic waves transmitted from the transmission unit 18 can be converged by the acoustic lens 24 at a position adjusted corresponding to a difference in timing at which each of the oscillators 17 transmits an ultrasonic wave.

The catheter A includes the transmission unit 18, which is disposed at the distal end of the tube 10 having the lumen 15 and has an ultrasonic wave transmitting function, the reception unit 19, which is disposed at the distal end of the tube 10 and has an ultrasonic wave receiving function, and the acoustic lens 24, which is placed so as to cover only the transmission unit 18 among the transmission unit 18 and the reception units 19. Ultrasonic beams transmitted from the transmission unit 18 are converged by passing through the acoustic lens 24, and a reflected wave reflected on biological tissue is received by the reception unit 19 without passing through the acoustic lens 24. Since setting of the positions, number, and the like of the reception units 19 is not bound by the position, size, and the like of the acoustic lens 24, the positions, number, and the like of the reception units 19 can be appropriately set to improve ultrasonic reception efficiency.

The reception units 19 are distributed at a plurality of locations. Such a configuration enables a plurality of the reception units 19 to receive reflected waves reflected on biological tissue and spreading in various directions, thus allowing improvement in resolution of an image of the biological tissue acquired on the basis of received information at the reception units 19.

Each of the transmission unit 18 and the reception unit 19 includes the oscillator 17, which has both of an ultrasonic wave transmitting function and an ultrasonic wave receiving function. The acoustic lens 24 is capable of shifting relative to the transmission unit 18 and the reception unit 19, in a manner of selectively covering only a part of the oscillators 17 among a plurality of the oscillators 17. Alternatively, a position of the acoustic lens 24 may be relatively shifted in the body by disposing the acoustic lens 24 fixed to the catheter A, and rotating the whole of the catheter A in a circumferential direction relative to the long axis of the catheter A. Relative displacement of a position of the acoustic lens 24 allows ultrasonic irradiation on one biological tissue from a plurality of different positions. In this way, a plurality of reception units 19 can provide multifaceted received information even when the biological tissue has a complex morphology. This allows improvement in resolution of an image of the biological tissue on the basis of received information at the reception units 19.

The catheter A has the lumen 15, which is inserted in the tube 10. The transmission unit 18 and the reception units 19 are arranged so as to surround the lumen 15. In other words, at least the reception units 19 among the transmission unit 18 and the reception units 19 are arranged so as to surround the lumen 15. Alternatively, the transmission unit 18 and the reception units 19 are arranged along the outer peripheral face of the catheter A in a cross section of the distal end portion of the catheter A. Such a configuration can provide information on biological tissue, which is a subject to be treated/examined by a medical device inserted in the lumen 15, from all directions of the biological tissue. This allows improvement in resolution of an image of the biological tissue acquired on the basis of received information at the reception units 19.

The transmission unit 18 has a row of a plurality of the oscillators 17, and has an ultrasonic wave transmitting function. Once different timing of ultrasonic wave transmission is made among the plurality of the oscillators 17, a plurality of ultrasonic waves can be converged to form a converged ultrasonic wave. The convergence position of the plurality of ultrasonic waves can be freely altered by changing the timing of ultrasonic wave transmission, thus allowing acquisition of much information on the biological tissue. Although FIG. 2 depicts that the transmission unit 18 and the reception unit 19 are placed so as to arrange a plurality of the oscillators 17 in a radial direction in a cross section of the catheter A, the plurality of the oscillators 17 may be arranged in a circumferential direction.

Figure 4:
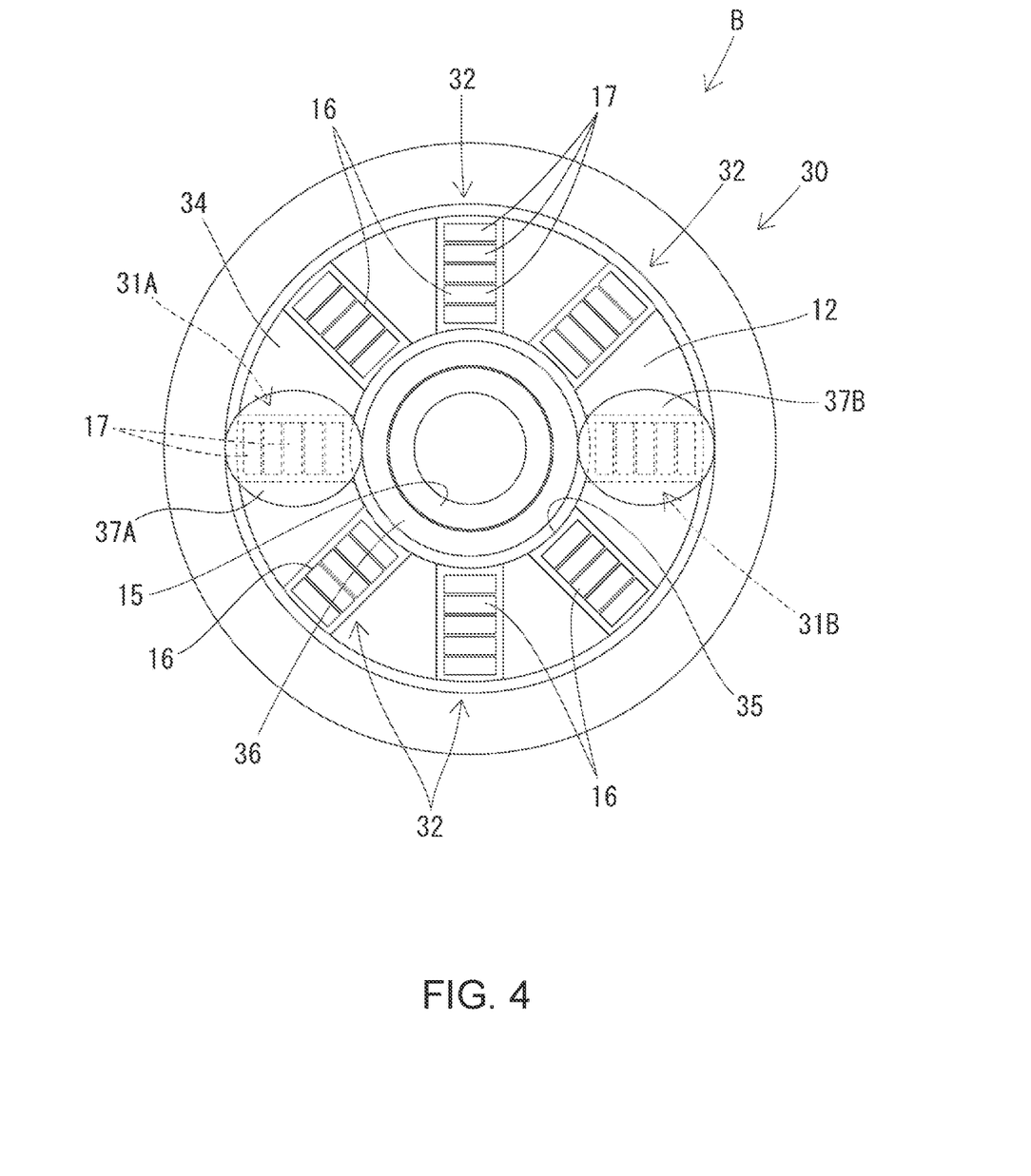
FIG. 4 is a front elevation view of a catheter of the disclosed embodiments.

Next, another exemplary embodiment will now be described with reference to FIG. 4. A catheter B in in the present embodiment has a configuration of transmission units 31A and 31B, reception units 32, and acoustic lenses 37A and 37B different from that of the catheter A. Since other configurations are the same as those of the catheter A, the same configurations are provided with a common numeral reference, with description omitted for a structure, an action, and an effect. The front end and the distal end in the catheter B are used synonymously.

The catheter B has one tube 30, which has flexibility, the lumen 15, which is formed in the tube 30, eight ultrasonic sensors 16, and a first and second ones of two of the acoustic lenses 37A and 37B. The inner tube 11, which constitutes the tube 30, the support plate portion 12, which is formed at the distal end of the inner tube 11, the eight ultrasonic sensors 16, which are attached to the front face of the support plate portion 12, and the lumen 15 are the same as those of the catheter A. Each of the ultrasonic sensors 16 can be switched between functioning as a first and second ones of two of the transmission units 31A and 31B, which transmit ultrasonic waves, and the reception unit 32, which receive ultrasonic waves.

A disc plate 34, which has a central hole 35, is attached to the distal end of an outer tube 33. The distal end of the lumen 15 is connected to form a pass-through, to an annular guide ring 36, which is fixed to the central hole 35 in the plate 34. The plate 34 covers the eight ultrasonic sensors 16 from the front side, i.e., the distal end side.

The plate 34 forms therein the first acoustic lens 37A and the second acoustic lens 37B, which are arranged so as to form a pair the lumen 15 interposed therebetween in the front view. When the outer tube 33 and the inner tube 11 relatively rotate in a circumferential direction coaxially, a pair of the acoustic lenses 37A and 37B rotates relative to the eight ultrasonic sensors 16. The pair of the acoustic lenses 37A and 37B selectively covers only any two of the ultrasonic sensors 16 that are to function as the first and second transmission units 31A and 31B, among the eight ultrasonic sensors 16. The first acoustic lens 37A covers the first transmission unit 31A, and the second acoustic lens 31 covers the second transmission unit 31B.

The two ultrasonic sensors 16, which function as the first and second transmission units 31A and 31B, may be controlled in a phased array system that transmits ultrasonic waves with time lag from the plurality of the oscillators 17. The plurality of the oscillators 17, which constitute the two transmission units 31A and 31B, are arranged so as to form a row with the lumen 15 interposed therebetween. Respective secondary waves transmitted from the first transmission unit 31A and the second transmission unit 31B are converged by passing through the first acoustic lens 37A and the second acoustic lens 37B, and irradiated at various angles on biological tissue (depiction omitted), which is a subject to be treated/examined, in front of the lumen 15. The oscillator 17 in six ultrasonic sensors 16, which function as the reception units 32, receives an ultrasonic wave reflected on the biological tissue.

The catheter B has the first transmission unit 31A and the second transmission unit 31B, which are arranged so as to form a pair with the lumen 15 interposed therebetween. The first transmission unit 31A is covered with the first acoustic lens 37A, and the second transmission unit 31B is covered with the second acoustic lens 37B. Such a configuration allows irradiation of two ultrasonic waves from two opposite directions on biological tissue, which is a subject to be treated/examined by a medical device inserted in the lumen 15.

Meanwhile, when ultrasonic waves are irradiated from one direction with respect to a medical device inserted in the lumen 15, a shade of the medical device is generated to represent an area not irradiated with ultrasonic waves. However, the configuration described above allows irradiation of ultrasonic waves from two opposite directions, thereby providing a smaller area to be in the shade of the medical device. This enables acquisition of multifaceted received information of biological tissue even when the biological tissue has a complex morphology. This allows improvement in resolution of an image of the biological tissue acquired on the basis of received information of the reception unit 32. Additionally, since biological tissue receives ultrasonic irradiation from two directions, it is only necessary to make a control such as providing the transmission units 31A and 31B with separate transmission timing, for the purpose of reducing attenuation or amplification due to a gap between phases of ultrasonic waves that separately arrived at the biological tissue.

Figure 5:
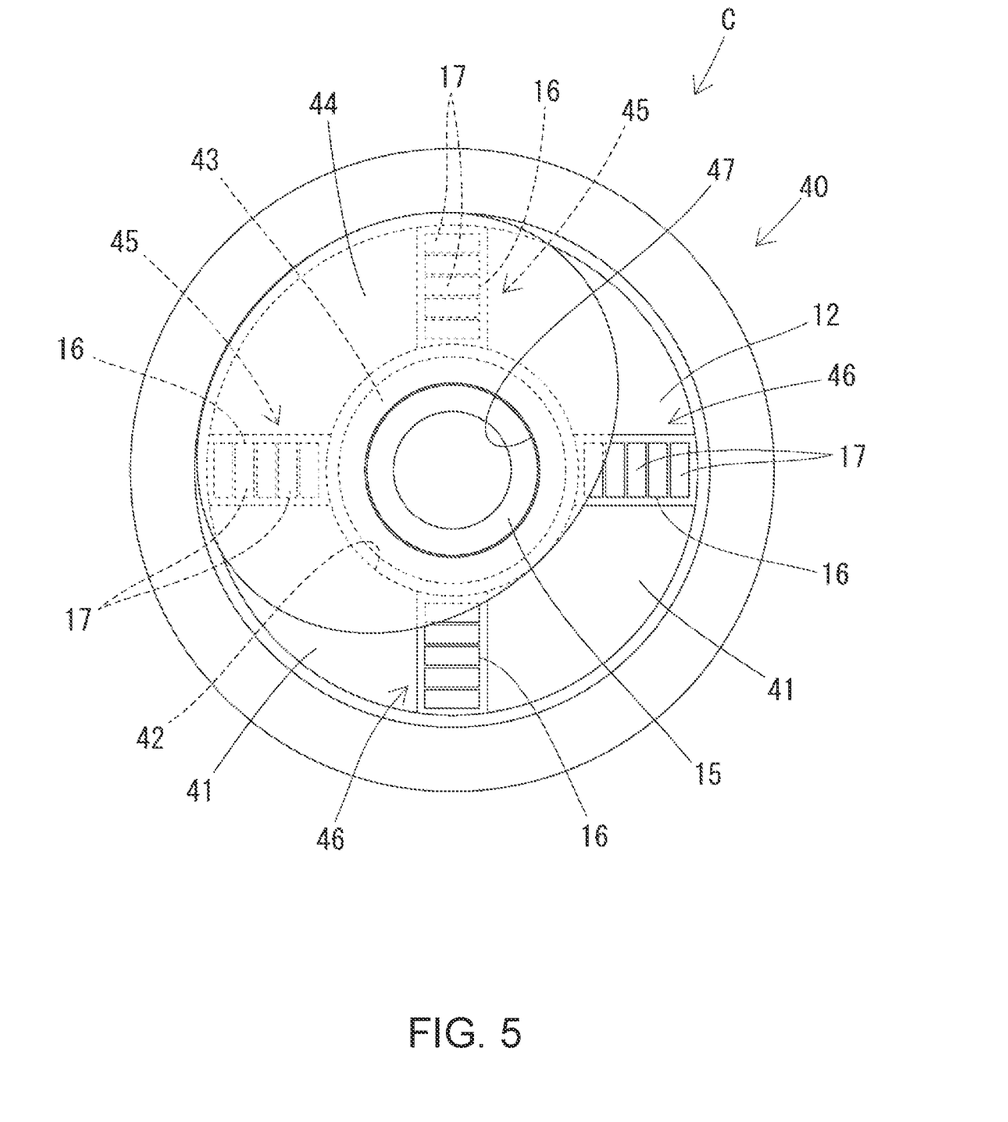
FIG. 5 is a front elevation view of a catheter of the disclosed embodiments.

Another exemplary embodiment will be described with reference to FIG. 5. A catheter C in the present embodiment has a configuration of a transmission unit 45, a reception unit 46, and an acoustic lens 44 different from that of the catheter A. Since other configurations are the same as those of the catheter A, the same configurations are provided with a common numeral reference, with description omitted for a structure, an action, and an effect.

The catheter C has one tube 40, which has flexibility, the lumen 15, which is formed in the tube 40, four ultrasonic sensor 16, and one acoustic lens 44. The inner tube 11, which constitutes the tube 40, the support plate portion 12, which is formed at the distal end of the inner tube 11, the four ultrasonic sensors 16, which are attached to the front face of the support plate portion 12, and the lumen 15 are the same as those of the catheter A. Each of the ultrasonic sensors 16 can switch between functioning as a transmission unit 45, which transmits ultrasonic waves, and a reception unit 46, which receives ultrasonic waves.

A disc plate 41 having a central hole 42 is attached to the distal end of the outer tube 40. The lumen 15 passes through an annular guide ring 43 fixed to the central hole 42 in the plate 41. The plate 41 covers the four ultrasonic sensors 16 from the front side, i.e., from the distal end side.

The plate 41 forms therein the acoustic lens 44, which forms a substantially elliptic shape in the front view. In the front view, an area forming the acoustic lens 44 includes any two of the ultrasonic sensors 16, which lie next to each other in a circumferential direction among the four ultrasonic sensors 16, and the lumen 15. The acoustic lens 44 forms therein a through-hole 47, which connects to the lumen 15 passing therethrough. When the outer tube 40 and the inner tube 11 relatively rotate in a circumferential direction coaxially, the acoustic lens 44 rotates relative to the four ultrasonic sensors 16 with respect to the center of the lumen 15. The acoustic lens 44 selectively covers only any two of the ultrasonic sensors 16, which are to function as the transmission units 45, among the four ultrasonic sensors 16.

Two ultrasonic sensors 16, which function as the transmission units 45, may be each controlled in a phased array system where ultrasonic waves are transmitted with time lag from a plurality of the oscillators 17. Respective secondary waves transmitted from the two transmission units 45 are converged by passing through the acoustic lens 44, and irradiated at various angles on biological tissue, which is a subject to be treated/examined, in front of the lumen 15. The oscillators in the two ultrasonic sensors 16, which function as the reception units 46, receive ultrasonic waves reflected on the biological tissue.

Another exemplary embodiment will be described with reference to FIG. 6. A catheter D in the present embodiment has a configuration of a transmission unit 55, a reception unit 56, and an acoustic lens 58 different from that of the catheter A. Since other configurations are the same as those of the catheter A, the same configurations are provided with a common numeral reference, with description omitted for a structure, an action, and an effect.

The catheter D has one tube 50, which has flexibility, the lumen 15, which is formed in the tube 50, seven ultrasonic sensors 16, and one acoustic lens 58. The tube 50 has a form containing coaxially an inner tube 51 inside an outer tube 52, with the inner tube 51 and the outer tube 52 being restricted to relatively shift with respect to each other in a radial direction. The inner tube 51 and the outer tube 52 are configured to be capable of relatively rotating in a circumferential direction and closely sliding within the coaxial form, by manipulation at the proximal end of the catheter D (depiction omitted).

The inner tube 51 has a circular shape in a cross section when cut perpendicular to the longitudinal direction. The distal end of the inner tube 51 is integrally formed with a support plate portion 53, which forms a circular shape concentric with the inner tube 51. The outer peripheral edge of the support plate portion 53 is connected to the inner periphery of the inner tube 51. In a position offset from the center of the support plate portion 53, an offset hole 54 is formed passing through the support plate portion 53. To the offset hole 54, the lumen 15, inserted in the inner tube 51, is connected to form a pass-through.

The seven ultrasonic sensors 16 are attached to the front face of the support plate portion 53. In a front view as the catheter D is seen from the distal end side in the longitudinal direction (see FIG. 6), the seven ultrasonic sensors 16 are arranged at an equal angle pitch of 45° in the circumferential direction concentric with the support plate portion 53. In the circumferential direction, the region including the seven ultrasonic sensors 16 is a region without interference with the offset hole 54 and the lumen 15. The lumen 15 and the seven ultrasonic sensors 16 lie at an equal angle pitch of 45° in the circumferential direction.

The seven ultrasonic sensors 16 are the same as those in the catheter A. Each of the ultrasonic sensors 16 can be switched between functioning as the transmission unit 55, which transmits ultrasonic waves, and the reception unit 56, which receives ultrasonic waves. Each of the ultrasonic sensors 16 is configured including a row of a plurality of oscillators 17 in a radial direction. The plurality of the oscillators 17, which constitute one of the ultrasonic sensors 16, lie in a row along a radial direction from the center of the support plate portion 53.

To the distal end of the outer tube 52, the plate 57 is fixed so as to integrally rotate with the outer tube 52. The plate 57 forms a projection from only a certain part in a circumferential direction on the inner peripheral face of the outer tube 52, the projection projecting inward in a radial direction perpendicular to the longitudinal direction of the outer tube 52. The board thickness direction of the plate 57 is parallel to the longitudinal direction of the outer tube 52. The projection dimension of the plate 57 from the outer tube 52 is less than the radial dimension of the support plate portion 53, and larger than the length dimension in a radial direction of one of the ultrasonic sensors 16. The circumferential width dimension of the plate 57 is set so as to be capable of covering the whole of one of the ultrasonic sensors 16, and incapable of covering simultaneously two of the ultrasonic sensors 16.

The plate 57 forms therein the acoustic lens 58. In the front view, the acoustic lens 58 has a substantially elliptical shape with a size to cover from the front only any one of the ultrasonic sensors 16 among the seven ultrasonic sensors 16. When the outer tube 52 and the inner tube 51 relatively rotate in a circumferential direction coaxially, the acoustic lens 58 rotates relative to the seven ultrasonic sensors 16 and the lumen 15 in a circumferential direction. The rotational range of the outer tube 52 relative to the inner tube 51 is a range where the plate 57 does not interfere with a medical device (depiction omitted) inserted in the lumen 15.

Figure 6:
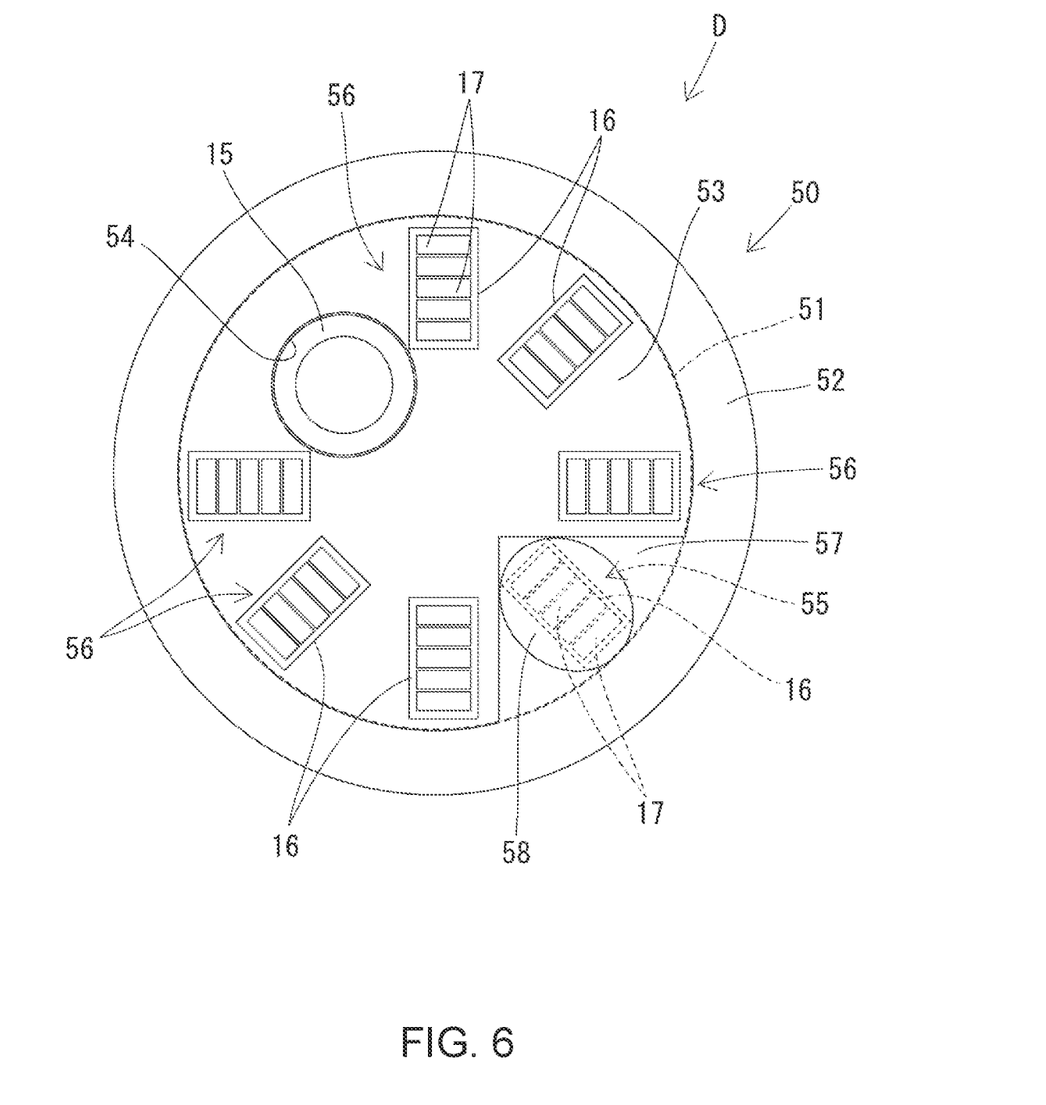
FIG. 6 is a front elevation view of a catheter of the disclosed embodiments.

In particular, when the outer tube 52 rotates relative to the inner tube 51 in a clockwise direction in FIG. 6, the maximum rotation range is limited to a position where the clockwise front side edge among a pair of radially extending side edges of the plate 57 comes in contact with a medical device. When the outer tube 52 rotates relative to the inner tube 51 in a counterclockwise direction in FIG. 6, the maximum rotation range is limited to a position where the counterclockwise front side edge among a pair of radially extending side edges of the plate 57 comes in contact with a medical device.

When the catheter D is used to diagnose the morphology of biological tissue (depiction omitted), the inner tube 51 and the outer tube 52 are relatively rotated by way of manipulation at the proximal end of the catheter D. This manipulation causes the acoustic lens 58 to cover one of the ultrasonic sensors 16 that functions as the transmission unit 55 among the seven ultrasonic sensors 16. Six of the ultrasonic sensors 16, which are not covered with the acoustic lens 58, function as the reception units 56. In the front face of the distal end of the catheter D, the one transmission units 55 and the six reception units 56 lie at equal pitch in a circumferential direction.

The ultrasonic sensor 16, which functions as the transmission unit 55, may be controlled in a phased array system where ultrasonic waves are transmitted with time lag from a plurality of the oscillators 17. Secondary waves transmitted from a plurality of the oscillators 17, which function as the transmission units 55, are converged in front of the lumen 15 by passing through the acoustic lens 58, and irradiated on biological tissue, which is a subject to be treated/examined. The oscillators 17 of the six ultrasonic sensors 16, which function as the reception units 56, receive ultrasonic waves reflected on biological tissue.

The disclosed embodiments are not limited to the embodiments illustrated by the aforementioned description and the drawings, and for example, the embodiments described below fall within the technical scope of the disclosure.

The above-discussed embodiments provide a structure where an ultrasonic sensor includes an arrangement of a plurality of the oscillators 17 in a row in a radial direction of a catheter, but a plurality of oscillators may be arranged in an array, and may also be arranged in an array on the whole cross sectional face of a catheter or the like. By arrangement of a plurality of oscillators in an array, traveling directions of secondary waves transmitted from a plurality of the oscillators 17 can be adjusted not only in a radial direction of the catheter as described above but also in a circumferential direction thereof.

The above discussed embodiments provide examples in which an acoustic lens is movable relative to an ultrasonic sensor, but an ultrasonic sensor and an acoustic lens may be relatively fixed as long as they are movable relative to biological tissue, which is a subject to be irradiated. For example, manipulation at the proximal end portion of a catheter causes the distal end portion of the catheter including an ultrasonic sensor and an acoustic lens to rotate on the long axis of the catheter, thus being movable relative to biological tissue. Mobility of a transmission unit formed with an ultrasonic sensor and an acoustic lens relative to biological tissue allows ultrasonic irradiation on biological tissue from various angles. In addition, even when a converged, irradiated ultrasonic wave is reflected at a variety of angles corresponding to a geometry of the biological tissue, the reflected ultrasonic waves are received by ultrasonic sensors that function as a plurality of reception units, thus allowing capturing of the geometry of the biological tissue with only a small amount of ultrasonic irradiation.

The above-discussed embodiments provide a transmission unit configured with a plurality of oscillators, but the transmission unit may be configured with only one oscillator.

The above-discussed embodiments provide a reception unit configured with a plurality of oscillators, but the reception unit may be configured with only one oscillator.

The above-discussed embodiments show that an oscillator constituting a transmission unit has both of an ultrasonic transmitting function and an ultrasonic receiving function, but an oscillator constituting a transmission unit may have only an ultrasonic transmitting function and no ultrasonic receiving function.

The above discussed embodiments show that an oscillator constituting a reception unit has both of an ultrasonic transmitting function and an ultrasonic receiving function, but an oscillator constituting a receiver part may have only an ultrasonic receiving function and no ultrasonic transmitting function.

The above-discussed embodiments show that a plurality of reception units receives reflected waves, but the number of reception units may be only one. In this case, reception efficiency of reflected waves is improved when a plurality of oscillators constituting one reception unit is arranged so as to line up over a wide range in both of a radial direction and a circumferential direction.

The above-discussed embodiments show that a plurality of oscillators constituting one ultrasonic sensor is arranged so as to line up in a radial direction, but a plurality of oscillators constituting one ultrasonic sensor may be arranged in a circumferential direction.

The above-discussed embodiments show that a plurality of ultrasonic sensors is arranged so as to line up in a circumferential direction, but a plurality of ultrasonic sensors may be arranged so as to line up in a radial direction. In this case, a plurality of oscillators constituting one ultrasonic sensor may be arranges so as to line up in a circumferential direction, or in a radial direction.

The above-discussed embodiments provide one lumen inserted in one catheter, but a plurality of lumens may be inserted in one catheter.

In the catheters A-C, an inner tube rotates while closely sliding on the inner periphery of an outer tube, but an inner tube may rotate relative to an outer tube while closely sliding on the outer periphery of a lumen. In this case, a support plate portion takes a flange form projected from the outer peripheral face of the inner tube in a radial direction.

In the catheters A-C, in addition to an inner tube being formed so as to closely slide on the inner periphery of an outer tube, an ultrasonic sensor is disposed in the inner tube and an acoustic lens disposed in the outer tube. However, in addition to an inner tube formed so as to closely slide on the outer periphery of a lumen, an ultrasonic sensor in an outer tube and an acoustic lens in the inner tube may be disposed.

In the catheters A and B, all of a plurality of the reception units are arranged so as to surround a lumen, but only a part of the reception units among a plurality of reception units may surround a lumen.

In the catheters A and B, eight ultrasonic sensors are disposed in one catheter, but the number of ultrasonic sensors disposed in one catheter may be seven or less or nine or more.

In the catheter A, one acoustic lens covers one ultrasonic sensor, but a plurality of acoustic lenses may cover a plurality of ultrasonic sensors respectively. In this case, a plurality of ultrasonic sensors covered with an acoustic lens and functioning as transmission units may be arranged so as to adjoin one another in a circumferential direction, or arranged so as to interpose an ultrasonic sensor that functions as a reception unit in a circumferential direction.

In the catheter C, four ultrasonic sensors are disposed in one catheter, but the number of ultrasonic sensors disposed in one catheter may be three or less or five or more.

In the catheter C, two ultrasonic sensors are covered with one acoustic lens, but the number of ultrasonic sensors covered with one acoustic lens may be one or may be three or more.

In the catheter C, two ultrasonic sensors are covered with one acoustic lens and are arranged so as to adjoin one another in a circumferential direction, but two ultrasonic sensors covered with one acoustic lens and functioning as transmission units may be arranged so as to interpose an ultrasonic sensor that functions as a reception unit in a circumferential direction.

In the catheter D, seven ultrasonic sensors are disposed in one catheter, but the number of ultrasonic sensors disposed in one catheter may be six or less or eight or more.

In the catheter D, one ultrasonic sensor is covered with an acoustic lens, but the number of ultrasonic sensors covered with an acoustic lens may be plural. In this case, a plurality of ultrasonic sensors covered with an acoustic lens and functioning as transmission units may be arranged so as to adjoin one another in a circumferential direction, or may be arranged so as to interpose an ultrasonic sensor that functions as a reception unit in a circumferential direction.

DESCRIPTION OF REFERENCE NUMERALS

A, B, C, D catheter
10, 30, 40, 50 tube
15 lumen
17 oscillator
18, 45, 55 transmission unit
19, 32, 46, 56 reception unit
24, 44, 58 acoustic lens
31A first transmission unit
31B second transmission unit
37A first acoustic lens
37B second acoustic lens

The invention claimed is:

1. A catheter comprising:
   a tube;
   at least one transmission unit disposed at a distal end of the tube and comprising a first ultrasonic sensor, the transmission unit being configured to transmit ultrasonic waves;
   at least one reception unit disposed at the distal end of the tube and comprising a second ultrasonic sensor, the reception unit being configured to receive reflected waves of ultrasonic waves transmitted from the transmission unit; and
   at least one acoustic lens disposed so as to cover only the transmission unit among the transmission unit and the reception unit,
   wherein:
   each of the first ultrasonic sensor and the second ultrasonic sensor includes an oscillator configured to both transmit and receive ultrasonic waves,
   the acoustic lens is movable relative to the transmission unit and the reception unit, in a manner of selectively covering only a portion of all the oscillators,
   the tube includes a first tube and a second tube that rotate relative to each other,
   the acoustic lens rotates integrally with the first tube, and
   the transmission unit and the reception unit rotate integrally with the second tube.

2. The catheter according to claim 1, wherein the at least one reception unit includes a plurality of reception units distributed at a plurality of locations at the distal end of the tube.

3. The catheter according to claim 2, wherein the at least one transmission unit is localized at only one position at the distal end of the tube.

4. The catheter according to claim 2, further comprising:
   a lumen disposed inside the tube,
   wherein the plurality of reception units are disposed so as to surround the lumen in a circumferential direction of the lumen.

5. The catheter according to claim 1, further comprising:
   a lumen disposed inside the tube,
   wherein:
   the at least one transmission unit includes a first transmission unit and a second transmission unit arranged with the lumen interposed therebetween in a radial direction of the lumen, and
   the at least one acoustic lens includes a first acoustic lens that covers the first transmission unit, and a second acoustic lens that covers the second transmission unit.

6. The catheter according to claim 1, wherein the first ultrasonic sensor comprises a row of a plurality of oscillators configured to transmit ultrasonic waves.

* * * * *